(12) United States Patent
Hoffman (10) Patent No.: US 11,097,234 B2
(45) Date of Patent: Aug. 24, 2021

(54) HIGH-SPEED CENTRIFUGAL MIXING DEVICES AND METHODS OF USE

(71) Applicant: Tyme, Inc., Wilmington, DE (US)

(72) Inventor: Steven Hoffman, Mahwah, NJ (US)

(73) Assignee: TYME, INC., Wilmington, DE (US)

( * ) Notice: Subject to any disclaimer, the term of this patent is extended or adjusted under 35 U.S.C. 154(b) by 870 days.

(21) Appl. No.: 15/635,320

(22) Filed: Jun. 28, 2017

(65) Prior Publication Data
US 2017/0296990 A1    Oct. 19, 2017

Related U.S. Application Data (62) Division of application No. 14/059,837, filed on Oct. 22, 2013, now Pat. No. 9,724,657.

(51) Int. Cl.
*B01F 9/00*      (2006.01)
*B01F 13/00*    (2006.01)
(Continued)

(52) U.S. Cl.
CPC .......... *B01F 9/0003* (2013.01); *A61K 31/138* (2013.01); *A61K 31/198* (2013.01);
(Continued)

(58) Field of Classification Search
CPC .... B01F 9/0003; B01F 9/0001; B01F 9/0021; B01F 13/0052; B01F 3/18;
(Continued)

(56) References Cited

U.S. PATENT DOCUMENTS

| 1,011,929 A | 12/1911 | Ecaubert |
| 2,961,703 A | 11/1960 | Pinotti |
| (Continued) | | |

FOREIGN PATENT DOCUMENTS

| JP | 58-183248 U | 12/1983 |
| JP | 64-2554 | 1/1989 |
| (Continued) | | |

OTHER PUBLICATIONS

BPAI Final Decision, Ex parte Kristensen, 10 U.S.P.Q.2d 1701, 1989.*

*Primary Examiner* — Charles Cooley
(74) *Attorney, Agent, or Firm* — BakerHostetler; Joseph Lucci (57) ABSTRACT

A centrifugal mixing device can include a shaft assembly that is operably coupled to a motor such that the motor rotates the shaft assembly about a first axis. The devices can further include a turret that is rotatably coupled to the shaft assembly such that the turret rotates about the first axis relative to the shaft assembly. The turret can include a first support, a first canister rotatably coupled to the first support such that the first canister rotates about a second axis, and a second canister rotatably coupled to the first support such that the second canister rotates about a third axis. The turret is configured to rotate about the first axis in a first rotational direction and each of the first and second canisters is configured to rotate about the second and third axes, respectively, in a second rotational direction that is opposite the first rotational direction.

19 Claims, 6 Drawing Sheets

(51) Int. Cl.
*B01F 3/18* (2006.01)
*A61K 31/366* (2006.01)
*A61K 31/138* (2006.01)
*A61K 31/506* (2006.01)
*A61K 31/436* (2006.01)
*A61K 31/198* (2006.01)

(52) U.S. Cl.
CPC .......... *A61K 31/366* (2013.01); *A61K 31/436* (2013.01); *A61K 31/506* (2013.01); *B01F 3/18* (2013.01); *B01F 9/0001* (2013.01); *B01F 9/0021* (2013.01); *B01F 13/0052* (2013.01); *B01F 2215/0032* (2013.01)

(58) Field of Classification Search
CPC .......... B01F 2215/0032; A61K 31/366; A61K 31/138; A61K 31/506; A61K 31/436; A61K 31/198
USPC .......... 366/209–219; 494/19; 433/49, 90, 91
See application file for complete search history.

(56) References Cited

U.S. PATENT DOCUMENTS

| | | | |
|---|---|---|---|
| 3,591,098 A | 7/1971 | McShirley | |
| 3,778,033 A | 12/1973 | Pullman | |
| 4,586,292 A * | 5/1986 | Carroll | B24B 11/00 366/219 |
| 5,029,760 A * | 7/1991 | Gamblin | B02C 17/08 241/137 |
| 5,167,448 A * | 12/1992 | Herold | B01F 9/0001 366/213 |
| 5,314,125 A | 5/1994 | Ohno | |
| 5,355,638 A * | 10/1994 | Hoffman | B24B 31/0212 451/32 |
| 5,531,637 A | 7/1996 | Kimura | |
| 5,551,779 A * | 9/1996 | Gantner | B01F 9/0001 366/217 |
| 6,086,242 A * | 7/2000 | Rajamani | B02C 17/08 241/171 |
| 6,361,486 B1 * | 3/2002 | Gordon | B04B 5/02 366/217 |
| 6,863,207 B2 | 3/2005 | Hoffman | |
| 7,201,512 B2 * | 4/2007 | Suzuki | B01F 11/0005 366/217 |
| 9,724,657 B2 * | 8/2017 | Hoffman | B01F 9/0003 |
| 10,722,818 B2 * | 7/2020 | Takaoka | B29B 7/106 |
| 2002/0132353 A1 | 9/2002 | Tamura et al. | |
| 2003/0053370 A1 * | 3/2003 | Murakami | B01F 9/003 366/217 |
| 2003/0103409 A1 * | 6/2003 | Mukasa | A61C 5/64 366/139 |
| 2005/0153426 A1 | 7/2005 | Muller | |
| 2007/0002682 A1 | 1/2007 | Vanderbilt et al. | |
| 2008/0193511 A1 * | 8/2008 | Massing | B82Y 5/00 424/450 |
| 2012/0106288 A1 * | 5/2012 | Harada | B01L 3/5021 366/75 |
| 2013/0183263 A1 | 7/2013 | Hoffman | |
| 2013/0184214 A1 | 7/2013 | Hoffman | |
| 2013/0343147 A1 | 12/2013 | Heinesen | |
| 2015/0110735 A1 * | 4/2015 | Hoffman | B01F 9/0003 424/85.2 |
| 2017/0296990 A1 * | 10/2017 | Hoffman | A61K 31/366 |
| 2021/0086148 A1 * | 3/2021 | Gross | B01F 9/0005 |

FOREIGN PATENT DOCUMENTS

| | | |
|---|---|---|
| JP | 03193127 | 8/1991 |
| JP | 6-42936 B2 | 6/1994 |
| JP | 2001276592 A | 10/2001 |
| JP | 2001340709 | 12/2001 |
| JP | 2004243158 | 9/2004 |
| JP | 2005-95573 | 4/2005 |
| JP | 2006043578 | 2/2006 |
| JP | 2006289254 | 10/2006 |
| JP | 4084493 | 4/2008 |
| JP | 2008264716 | 11/2008 |
| JP | 2009273959 A | 11/2009 |
| JP | 2010274171 | 12/2010 |
| JP | 2011050814 | 3/2011 |
| JP | 2011185693 | 9/2011 |
| TW | 200911357 A | 3/2009 |
| WO | WO-2013/109610 | 7/2013 |

* cited by examiner

HIGH-SPEED CENTRIFUGAL MIXING DEVICES AND METHODS OF USE

CROSS REFERENCE TO RELATED APPLICATIONS

This application is a divisional of U.S. application Ser. No. 14/059,837 filed Oct. 22, 2013 the entirety of which is incorporated by referenced herein.

TECHNICAL FIELD

The present inventions relate generally to centrifugal mixing devices, methods of using them, and mixtures produced by such methods.

BACKGROUND

Centrifugal processing devices have been used to separate liquids and/or to finish or otherwise smooth surfaces of different objects. Some of these processing devices have an outer vessel and a turret within the outer vessel that is rotated about the axis of the outer vessel. The turret includes at least one inner vessel that rotates about its own axis as the turret rotates about the axis of the outer vessel. In particular, a frictional force between the inner vessel and the outer vessel causes the inner vessel to rotate in a rotational direction that is opposite the rotational direction of the turret as the turret is rotated about the outer vessels axis. The contents of the inner vessels of such processing devices are subjected to an acceleration several hundred times that associated with gravity ("g"). While these devices are useful for finishing objects and/or separating liquids, their utility for applications such as processing particulate materials such as pharmaceuticals could be improved by increasing the acceleration to which their contents are subjected. Furthermore, there is a need for devices of this type in which substantially the same forces and accelerations act on the contents of the mixing device.

SUMMARY

The present invention provides centrifugal mixing devices, particularly those that are capable of repeatably forming mixtures of particulate materials.

In accordance with certain embodiments of the present invention, a centrifugal mixing device comprises a shaft assembly that is elongate along a first axis and is configured to be operably coupled to a motor such that the motor rotates the shaft assembly about the first axis. The device further comprises a turret that is rotatably coupled to the shaft assembly such that the turret is configured to rotate about the first axis relative to the shaft assembly. The turret can include a first support, a first canister rotatably coupled to the first support on a first side of the shaft assembly such that first canister rotates about a second axis, and a second canister rotatably coupled to the first support on a second side of the shaft assembly such that the second canister rotates about a third axis. The turret can be configured to rotate about the first axis in a first rotational direction and each of the first and second canisters are configured to rotate about the second and third axes, respectively, in a second rotational direction that is opposite the first rotational direction.

In accordance with other embodiments, the centrifugal mixing device comprises a shaft assembly that includes a shaft body that is elongate along a first axis and is configured to be operably coupled to a motor such that the motor rotates the shaft assembly about the first axis, and a first shaft pulley that is rigidly fixed to the shaft body. The device further comprises a turret that is rotatably coupled to the shaft body and includes a first canister that has a first canister pulley and is rotatable about a second axis, and a second canister that has a second canister pulley and is rotatable about a third axis. The device further comprises a first drive belt that is in communication with the first shaft pulley, the first canister pulley, and the second canister pulley such that rotation of the shaft assembly by the motor causes the first and second canisters to rotate about the second and third axes, respectively. The first shaft pulley, the first canister pulley, and the second canister pulley are each sized such that an acceleration of at least 600 g is imposed on material retained in the first and second canisters when the motor rotates the shaft assembly about the first axis.

In accordance with other aspects of the invention, methods of operating the device can comprise the steps of: providing a centrifugal mixing device having a shaft assembly and a turret coupled to the shaft assembly, the turret including a support that is rotatable about a first axis defined by the shaft assembly and a first canister that is rotatably coupled to the support such that the first canister rotates about a second axis; placing in said first canister at least three substantially spherical members, a first particulate material, and at least a second particulate material; rotating the turret about the first axis in a first direction at a first rotational speed; rotating the first canister about the second axis in a second direction opposite the first direction at a second rotational speed; causing each member to contact an inner surface within the first canister such that a substantially constant force is applied against the inner side surface as the turret rotates at the first rotational speed and as the first canister rotates at the second rotational speed; and causing the first and second particulates to move between the members and inner surface such that at least one of the first and second particulates is impregnated by the other.

Pharmaceutical compositions prepared by processes in accordance with the invention are also provided.

BRIEF DESCRIPTION OF THE DRAWINGS

The foregoing summary, as well as the following detailed description, will be better understood when read in conjunction with the appended drawings, which show exemplary embodiments for the purposes of illustration. It should be understood, however, that the application is not limited to the precise arrangements and systems shown. In the drawings.

DETAILED DESCRIPTION OF ILLUSTRATIVE EMBODIMENTS

The present subject matter may be understood more readily by reference to the following detailed description which forms a part of this disclosure. Unless otherwise defined herein, scientific and technical terms used in connection with the present application shall have the meanings that are commonly understood by those skilled in the art. Further, unless otherwise required by context, singular terms shall include pluralities and plural terms shall include the singular.

Certain terminology is used in the following description for convenience only and is not limiting. The words "right", "left", "lower" and "upper" designate directions in the drawings to which reference is made. The words "proximally" and "distally" refer to directions toward and away from, respectively, the specific component being described. The terminology includes the above-listed words, derivatives thereof, and words of similar import.

Figure 1A:
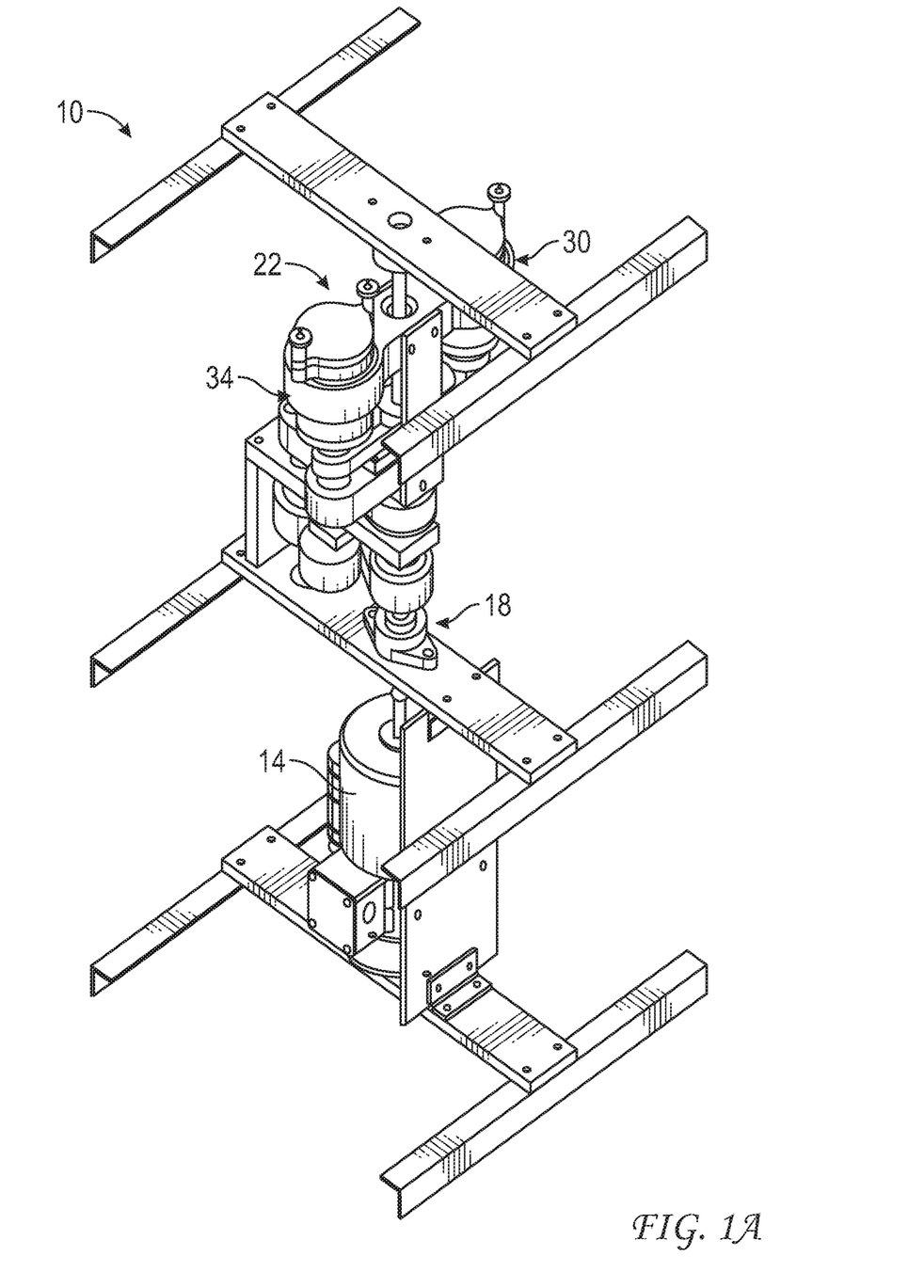
FIG. 1A is a top perspective view of a centrifugal mixing device in accordance with an embodiment of the invention, the centrifugal mixing device including a shaft assembly, a motor coupled to the shaft assembly, and a turret rotatably coupled to the shaft assembly.
Figure 1B:
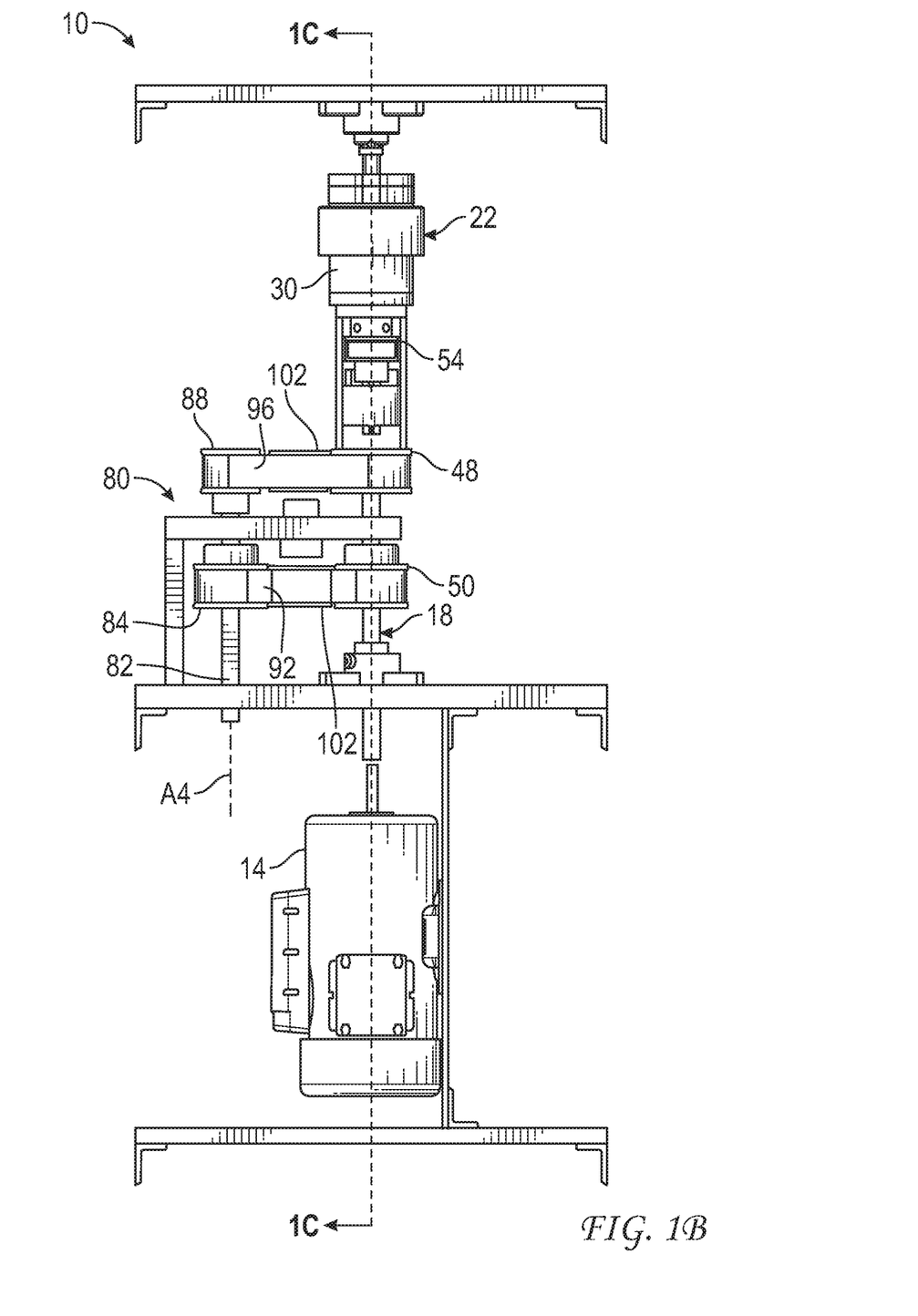
FIG. 1B is a side view of the centrifugal device shown in FIG. 1A.
Figure 1C:
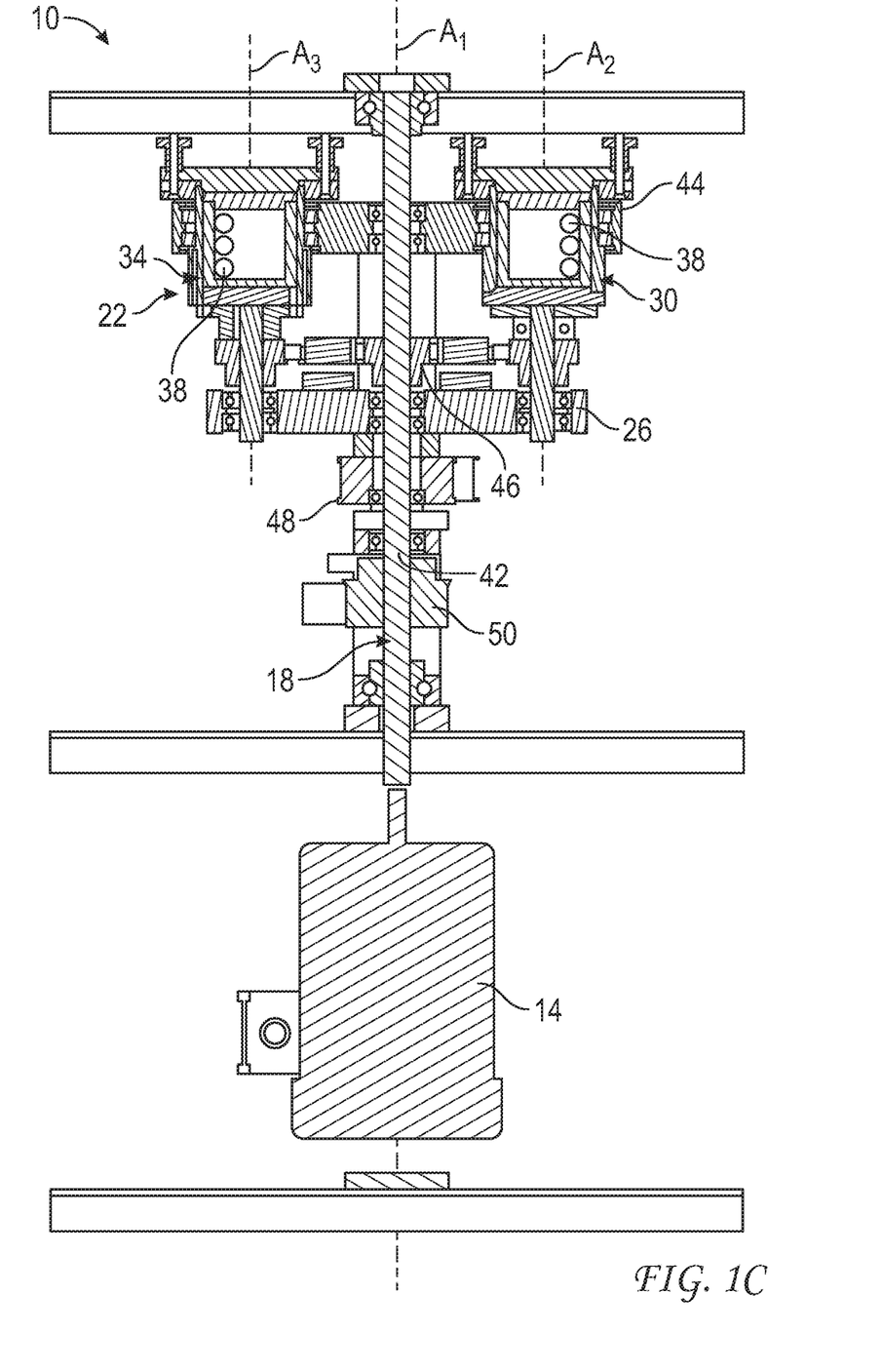
FIG. 1C is a cross-sectional view of the centrifugal device shown in FIG. 1B through the line 1C-1C and showing first and second canisters of the turret that are each configured to retain material.

Referring to FIGS. 1A-1C, a centrifugal mixing device 10 according to the invention can include a motor 14, a shaft assembly 18 that is elongate along a first axis $A_1$ and is operably coupled to the motor 14 such that the motor 14 rotates the shaft assembly 18 about the first axis $A_1$, and a turret 22 that is rotatably coupled to the shaft assembly 18 such that the turret 22 is configured to rotate about the first axis $A_1$ relative to the shaft assembly 18. As shown in FIG. 1C, the turret 22 includes a first support 26, a first canister 30 rotatably coupled to the first support 26 on a first side of the shaft assembly 18 and a second canister 34 rotatably coupled to the first support 26 on a second side of the shaft assembly 18. In the illustrated embodiment, the first and second canisters 30 and 34 are on opposed sides of the shaft assembly 18. It should be appreciated, however, that the first and second canisters 30 and 34 can be located on any side of the shaft assembly 18 and that the centrifugal mixing device 10 can include any number of canisters as desired. For example, the centrifugal mixing device 10 can include one canister or two or more canisters as desired.

With continued reference to FIG. 1C, the first canister 30 is configured to rotate about a second axis $A_2$ and the second canister 34 is configured to rotate about a third axis $A_3$ both of which are parallel to the first axis $A_1$. Each of the first and second canisters 30 and 34 is configured to receive at least three spherical members 38, a first particulate material, and at least a second particulate material. The turret 22 is configured to rotate about the first axis $A_1$ in a first rotational direction at a first rotational speed and each of the first and second canisters 30 and 34 are configured to rotate about the second and third axes $A_2$ and $A_3$, respectively, in a second rotational direction that is opposite the first rotational direction at second and third rotational speeds, respectively. Rotation of the turret 22 and the canisters 30 and 34 will cause each spherical member 38 to contact an inner surface within each canister 30 and 34 such that a substantially constant force is applied against the inner surfaces as the turret 22 rotates at the first rotational speed and as the first and second canisters 30 and 34 rotate at the second and third rotational speeds. The particulates within the first and second canisters 30 and 34 will move between the members 38 and the inner surfaces such that at least one of the first and second particulates is impregnated with the other. Typically, the softer of the particulates will be impregnated by the other(s). It should be appreciated, however, that the potential exists for the softer of two particulates to effect impregnation. In this regard, impregnation according to the present invention can involve, but does not require, a portion of one type of particulate extending into a portion of another type of particulate. For example, one type of particulate can be impregnated by another by fully surrounding or partially surrounding it. Thus, impregnation according to the present invention is effected where at least two different type of particulates are sufficiently conjoined that they exhibit the physical properties of a single type of particulate when exposed to normal material handling procedures such as sieving and pouring.

The centrifugal mixing device 10 is configured to reach high rotational speeds and can thus subject the contents of the first and second canisters 30 and 34 to a high accelerations. For example, the first rotational speed can be between about 100 rpm and about 1750 rpm and the second and third rotational speeds can be between about 140 rpm and about 2550 rpm. Preferably the first rotational speed is about 1750 rpm and the second and third rotational speeds are about 2500 rpm. It should be appreciated, however, that the first, second, and third rotational speeds can be the same or different from each other. It should be further appreciated that although it is preferred that the first and second canisters 30 and 34 rotate at the same rotational speed, the first and second canisters 30 and 34 can be configured to rotate at different speeds relative to teach other, as desired.

The centrifugal mixing device 10 is configured such that rotation of the turret 22 and the canisters 30 and 34 subjects the contents of the canisters 30 and 34 to an acceleration of at least 600 g. For example, the centrifugal mixing device 10 can be configured such that the contents of the canisters 30 and 34 are subjected to an acceleration of between about 600 g and about 750 g and preferably to an acceleration of about 691 g. The high acceleration that the contents experience and the substantially constant force provided by the spherical members 38 allow the centrifugal mixing device 10 to make certain pharmaceutical compositions. In certain embodiments, for example, melanin and/or a melanin promoter can be processed with one or more particulate cancer drugs. FDA-approved cancer drugs that are amenable to such processing include selective estrogen receptor modulators such as tamoxifen, toremifene (Fareston®), and fulvestrant (Faslodex®); aromatase inhibitors such as anastrozole (Arimidex®), exemestane (Aromasin®), and letrozole (Ferrara®); signal transduction inhibitors such as imatinib mesylate (Gleevec®), dasatinib (Sprycel®), nilotinib (Tasigna®), bosutinib (Bosulif®), lapatinib (Tykerb®), gefitinib (Iressa®), erlotinib (Tarceva®), temsirolimus (Torisel®), everolimus (Afinitor®), vandetanib (Caprelsa®), vemurafenib (Zelboraf®), and crizotinib (Xalkori®); drugs that modify the function of proteins that regulate gene expression and other cellular functions, such as vorinostat (Zolinza®), romidepsin (Istodax®), bexarotene (Targretin®), alitretinoin (Panretin®), tretinoin (Vesanoid®); drugs that induce cancer cells to undergo apoptosis, such as bortezomib (Velcade®), carfilzomib (Kyprolis™), and pralatrexate (Folotyn®); and drugs that interfere with angiogenesis, such as sorafenib (Nexavar®), sunitinib (Sutent®), pazopanib (Votrient®), Regorafenib (Stivarga®), and cabozantinib (Cometriq™). Additional cancer drugs amenable to the present invention include denileukin diftitox (Ontak®), ziv-aflibercept (Zaltrap®), cisplatin, cisplatinum, (cis-diamminedichloroplatinum(II)), carboplatin, oxaliplatin, benzyl isothiocyanate, acetylcholine, and dihydrotestosterone (DHT). It should be appreciated, however, that other drugs that exist in particulate form may be amenable to processing in accordance with the present invention.

Figure 2A:
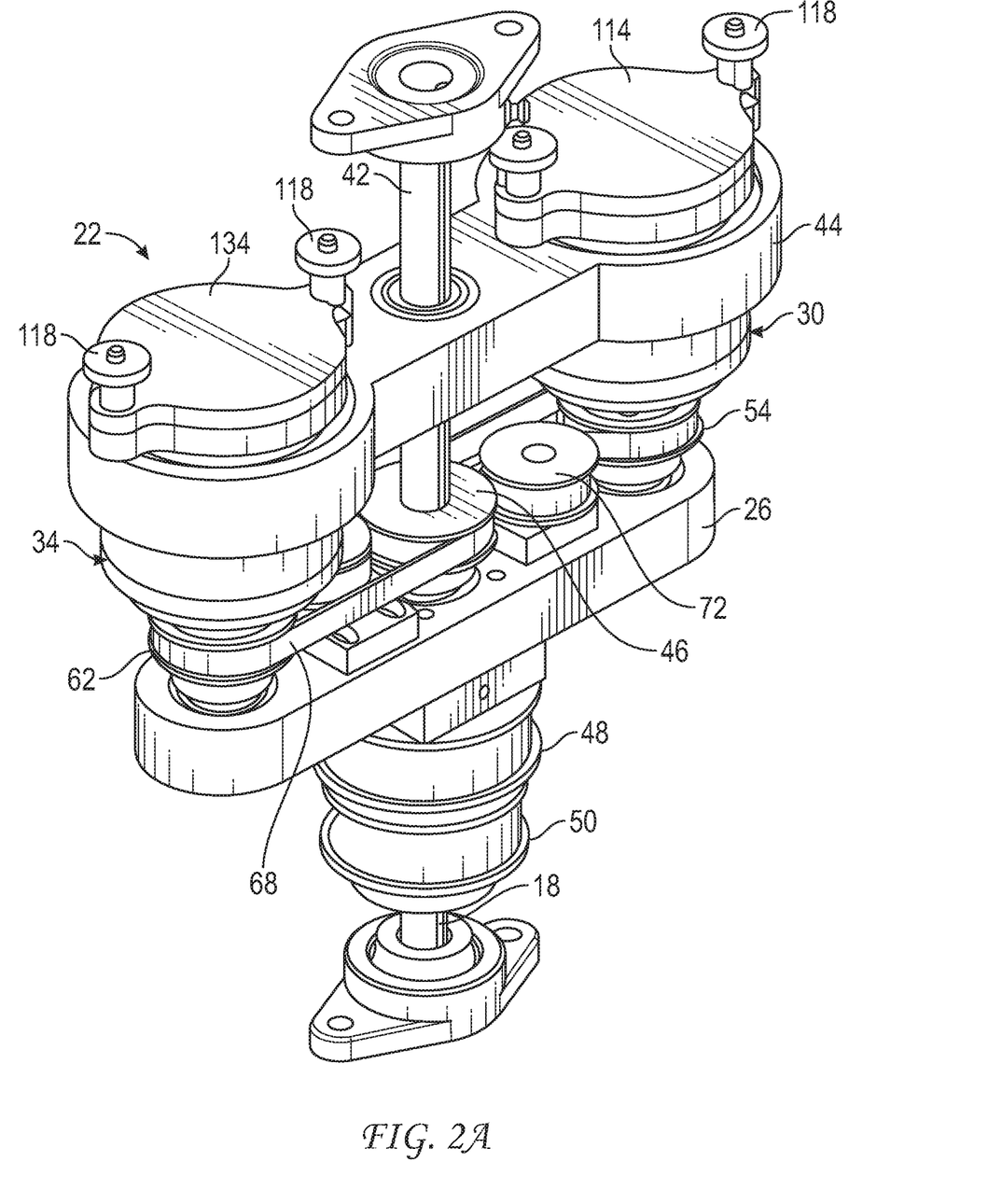
FIG. 2A is a perspective view of the turret and shaft assembly of the device shown in FIG. 1A.
Figure 2B:
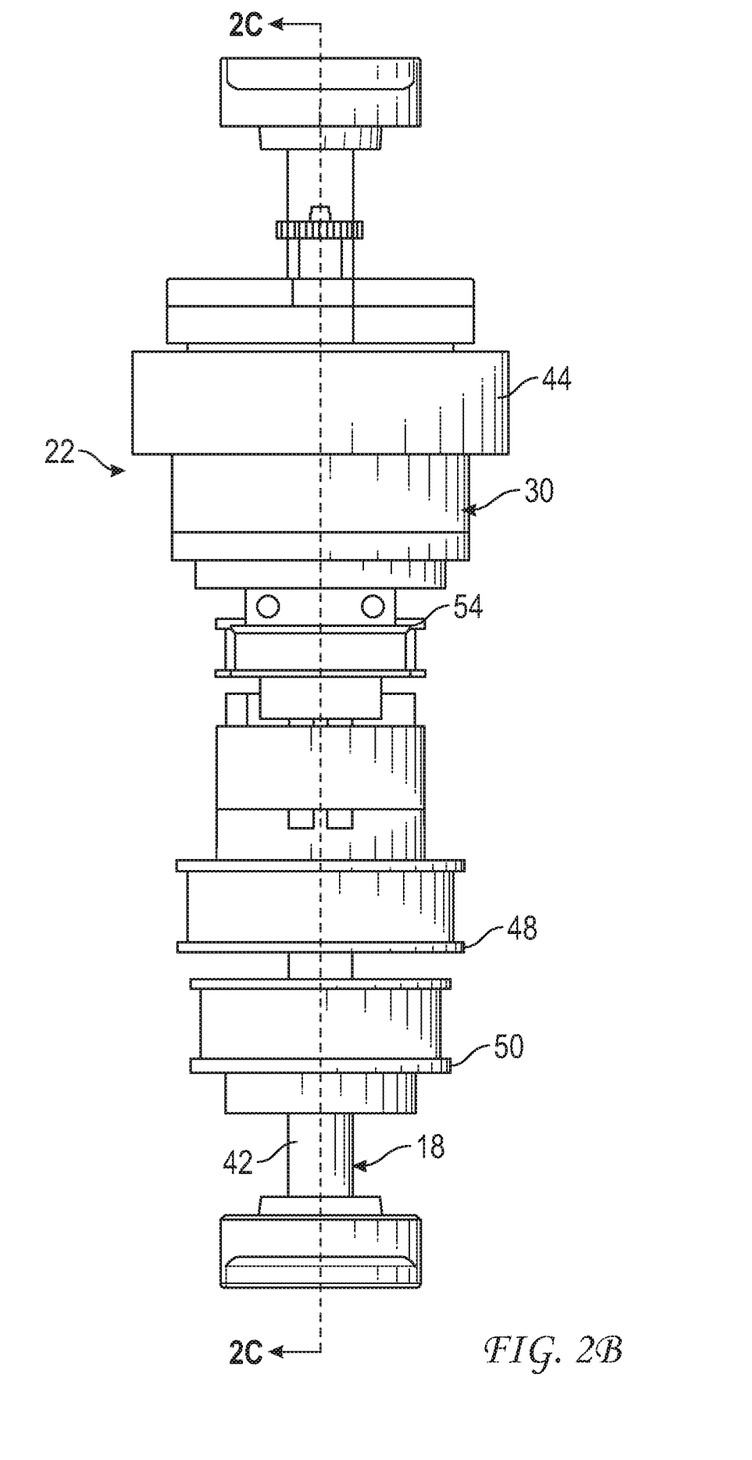
FIG. 2B is a side view of the turret and shaft assembly shown in FIG. 2A.
Figure 2C:
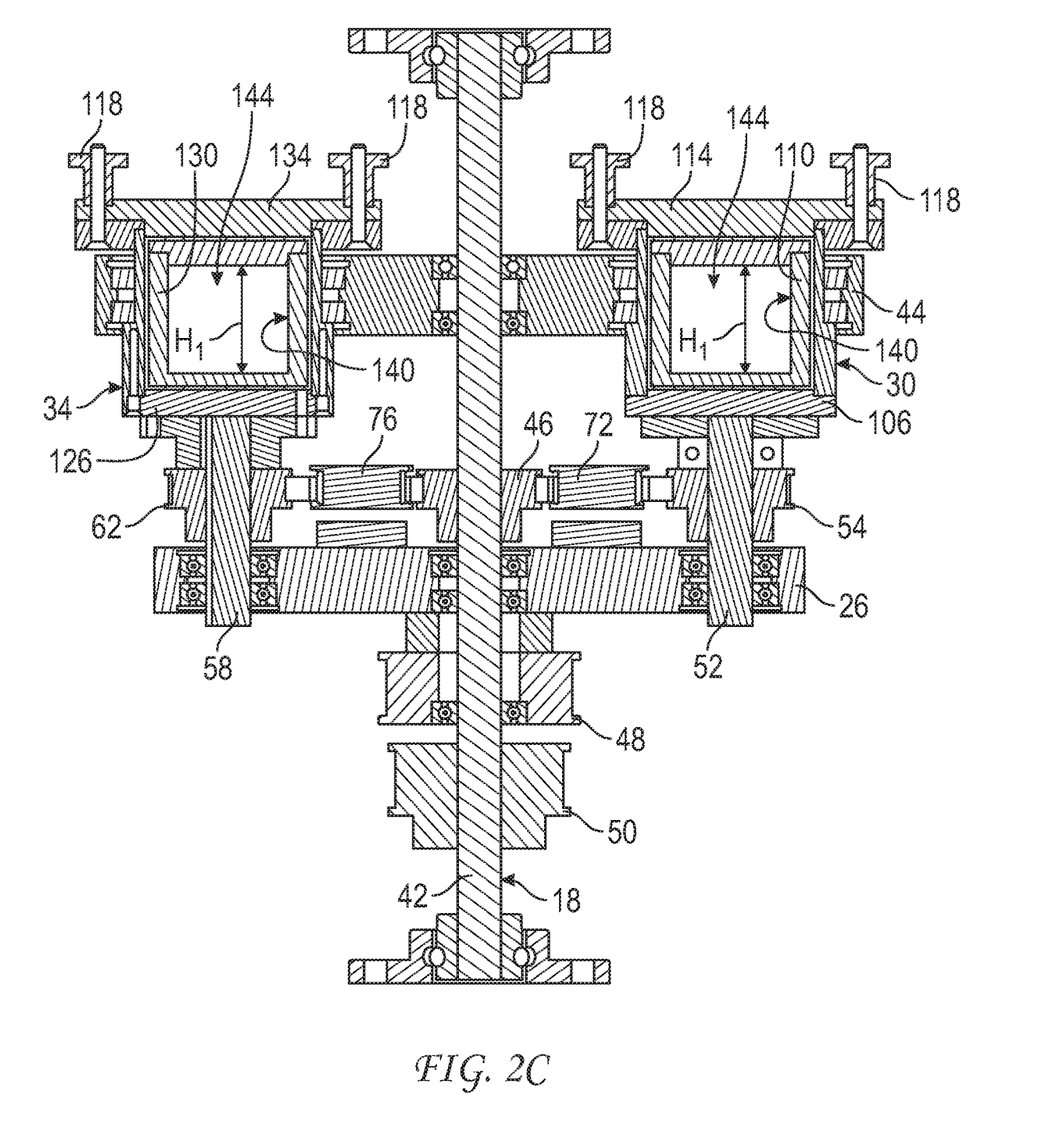
FIG. 2C is a cross-sectional view of the turret and shaft assembly shown in FIG. 2B through the line 2C-2C.

Now in reference to FIGS. 2A-2C, the shaft assembly 18 includes a shaft body 42 that is elongate along the first axis $A_1$, a first shaft pulley 46 fixed to the shaft body 42, and a second shaft pulley 50 fixed to the shaft body 42 and spaced from the first shaft pulley 46 along the first axis $A_1$. The first shaft pulley 46 is configured to be operatively coupled to the first and second canisters 30 and 34, for example, via a single belt such that as the shaft assembly 18 is rotated about the first axis $A_1$ by the motor 14, the first and second canisters 30 and 34 are driven to be rotated about the second and third axes $A_2$ and $A_3$, respectively, by the belt. Similarly, the second shaft pulley 50 is operatively coupled to the turret 22, for example via a series of belts, such that as the shaft assembly 18 is rotated about the first axis $A_1$ by the motor 14, the turret 22 is driven to be rotated about the first axis $A_1$ relative to the shaft body 42 by the series of belts. In this way a single motor can be used to drive the turret 22 to rotate about the first axis $A_1$ and separately drive the first and second canisters 30 and 34 to rotate about the second and third axes $A_2$ and $A_3$. It should be appreciated, however, that in some embodiments the canisters 30 and 34 can be driven by a separate motor or motors than the motor that causes the turret 22 to rotate, and that any number of belts can be used to transfer the rotational motion of the shaft assembly 18 to the turret 22 and to the first and second canisters 30 and 34.

With continued reference to FIGS. 2A-2C, the turret 22 further includes a second support 44 spaced from the first support 26 along the first axis $A_1$ and a turret pulley 48 that is rigidly coupled to the first support 26 and rotatably coupled to the shaft assembly 18 such that rotation of the turret pulley 48 causes the first and second supports 26 and 44 to rotate about the first axis $A_1$ relative to the shaft assembly 18. As shown in FIG. 2C, the first and second canisters 30 and 34 are rotatably coupled to the first and second supports 26 and 44. Thus, as the first and first and second supports 26 and 44 are rotated about the first axis $A_1$ the first and second canisters 30 and 34 are also rotated about the first axis $A_1$.

As shown in FIG. 2C, while rotating about the first axis $A_1$ the first canister 30 is configured to rotate about the second axis $A_2$ and the second canister 34 is configured to rotate about the third axis $A_3$. As shown, the first canister 30 includes a first canister shaft 52 that is rotatably coupled to the first support 26 and a first canister pulley 54 that is rigidly fixed to the first canister shaft 52. Similarly, the second canister 34 includes a second canister shaft 58 that is rotatably coupled to the first support 26 and a second canister pulley 62 that is rigidly fixed to the second canister shaft 58. The first and second canister pulleys 54 and 62 are positioned such that the first shaft pulley 46 is located between the first and second canister pulleys 54 and 62.

With continued reference to FIG. 2C, the centrifugal mixing device 10 further includes a first drive belt 68 that is in communication with the first shaft pulley 46 and the first and second canister pulleys 54 and 62 such that the first drive belt 68 drives the first and second canister pulleys 54 and 62 to rotate the first and second canisters 30 and 34 about the second and third axes $A_2$ and $A_3$, respectively when the motor 14 causes the first shaft pulley 46 to rotate about the first axis $A_1$. To maintain the first drive belt 68 in tension, the turret 22 further includes a first tension pulley 72 and a second tension pulley 76 also in communication with the first drive belt 68. As shown in FIG. 2C, the first tension pulley 72 is supported by the first support 26 between the first shaft pulley 46 and the first canister pulley 54 and the second tension pulley 76 is supported by the first support 26 between the first shaft pulley 46 and the second canister pulley 62. As shown in FIG. 2A, the first drive belt 68 is maintained in tension by the first and second tension pulleys 72 and 76 as it is placed in communication with the first shaft pulley 46 and the first and second canister pulleys 54 and 62. Therefore, as the first shaft pulley 46 drives the first drive belt 68, the first drive belt 68 will drive the first and second canister pulleys 54 and 62. In this way, the motor 14 can drive the first and second canister pulleys 54 and 62 to thereby cause the first and second canisters 30 and 34 to rotate about the second and third axes $A_2$ and $A_3$, respectively. Thus, rotation of the shaft assembly 18 is transferred to the first and second canisters 30 and 34.

Referring back to FIGS. 1A and 1B, the centrifugal mixing device 10 can further include a transition member 80 configured to transfer rotational motion of the shaft assembly 18 to the turret 22 to thereby cause the turret 22 to rotate about the first axis $A_1$ relative to the shaft body 42. As shown in FIG. 1B, the transition member 80 can include a transition shaft 82, a first transition pulley 84 fixed to the transition shaft 82, and a second transition pulley 88 fixed to the transition shaft 82 such that both the first transition pulley 84 and the second transition pulley 88 together rotate about a fourth axis $A_4$ when the shaft assembly 18 is driven by the motor 14. As illustrated, the mixing device 10 can further include a second drive belt 92 that is in communication with the second shaft pulley 50 and the first transition pulley 84 such that the second drive belt 92 drives the first transition pulley 84 to rotate the transition member 80 about the fourth axis $A_4$ when the motor 14 causes the second shaft pulley 50 to rotate about the first axis $A_1$. As further illustrated, the mixing device 10 can additionally include a third drive belt 96 that is in communication with the second transition pulley 88 and the turret pulley 48 such that the third drive belt 96 drives the turret pulley 48 to rotate the turret 22 about the first axis $A_1$ when the motor 14 causes the transition member 80 to rotate about the fourth axis $A_4$. As shown in FIG. 1B, the centrifugal mixing device 10 can further include a pair of tension pulleys 102 that maintain the second and third drive belts 92 and 96 in tension.

In the illustrated embodiment, the turret pulley 48, the first and second transition pulleys 84 and 88, the first and second shaft pulleys 46 and 50, and the first and second canister pulleys 54 and 62 each has a respective diameter such that an acceleration of at least 600 g, preferably between about 600 g and about 750 g, and even more preferably of about 691 g is imposed on material (e.g. the spherical members and particulates) retained in the first and second canister 30 and 34 when the motor 14 rotates the shaft assembly 18. Furthermore, the first, second, and third belts 68, 92, and 96 are oriented such that the turret 22 rotates in a first direction and the first and second canisters 30 and 34 rotate in a second direction that is opposite the first direction. It should be appreciated, however, that in certain embodiments the pulleys 46, 48, 50, 54, 62, 84, and 88 can have respective diameters that result in other operating parameters as desired and that the belts 68, 92, and 96 can be oriented such that the turret 22 and canisters 30 and 34 rotate in the same rotational direction. It should be further appreciated that the resultant desired parameters may depend on the size, type, and/or number of particulate materials being combined.

Referring back to FIG. 2C, the first canister 30 further includes a first canister housing 106 that is rigidly coupled to the first canister shaft 52 and rotatably coupled to the second support 44. Therefore, the first canister 30 can be rotatably supported by both the first and second supports 26 and 44. As shown in FIG. 2C, the first canister 30 can further include a first removable vessel 110 that is housed within the first canister housing 106 and a first lid 114 that is removably attached to the first canister housing 106 to thereby selectively retain the first removable vessel 110 within the first canister housing 106. The first lid 114 can be fixed to the first canister housing 106 with attachment members 118, illustrated as bolts. It should be appreciated, however, that the first lid 114 can be fixed to the first canister housing 106 with any attachment member as desired.

Similarly, the second canister 34 further includes a second canister housing 126 that is rigidly coupled to the second canister shaft 58 and rotatably coupled to the second support 44. Therefore, the second canister 34 can be rotatably supported by both the first and second supports 26 and 44. As shown in FIG. 2C, the second canister 34 can further include a second removable vessel 130 that is housed within the second canister housing 126 and a second lid 134 that is removably attached to the second canister housing 126 to thereby selectively retain the second removable vessel 130 within the second canister housing 126. The second lid 134 can be fixed to the second canister housing 126 with attachment members 118, illustrated as bolts. It should be appreciated, however, that the second lid 134 can be fixed to the first canister housing 126 with any attachment member as desired.

In the illustrated embodiment and as shown in FIGS. 1C and 2C, the first and second vessels 110 and 130 are each configured to retain the spherical members 38 and the at least two particulate materials. Each vessel 110 and 130 includes an inner surface 140 that defines a cavity 144 in which the materials can be retained. As shown in FIG. 2C, each inner surface 140 can be a side inner surface that defines a respective height $H_1$ measured from a bottom of the cavity 144 to a top of the cavity 144. The spherical members 38 are configured to contact and apply a substantially constant force against the inner surfaces 140 as the turret 22 rotates at the first rotational speed and as the first and second canisters 30 and 34 rotate at their respective rotational speeds. In particular the spherical members 38 are configured to contact the inner surfaces 140 so as to form a column or columns of members 38 that extend from the bottom of the inner surfaces 140 to the top of the inner surfaces 140 as shown in FIG. 1C. When in operation, the spherical members 38 maintain contact with the inner surfaces 140 and thus the force applied against the inner surfaces 140 by each spherical member 38 remains substantially constant. The size, weight, and material of the spherical members 38 can be such that the spherical members 38 form the columns and apply the desired force against the inner surfaces 140. The spherical members 38 can be made of ceramic and can each weigh about 25 grams. It should be appreciated, however, that the spherical members 38 can be made of any material as desired and can have any weight as desired. It should be further appreciated that the vessels 110 and 130 can be configured to retain any number of spherical members 38 as desired, so long as the spherical members 38 form a column(s) against the inner surfaces 140 such that each spherical member 38 contacts and applies a substantially constant force against the inner surface 140 of the canister in which it is retained. It should yet be further appreciated that the first and second canisters 30 and 34 can be void of the removable vessels 110 and 130 such that the canister housings 106 and 126 themselves receive the spherical members 38 and particulates.

In operation, as the turret rotates at the first rotational speed and as the first and second canisters 30 and 34 rotate at their respective rotational speeds, the first and second particulates within the canisters 30 and 34 will move between the spherical members 38 and inner surfaces 140 such that at least one of the first and second particulates is impregnated by the other. In particular, the particulates can continuously move between the spherical members 38 and the inner surfaces 140, and can have different orientations each time they move between the spherical members 38 and inner surfaces 140 to thereby cause at least one of the first and second particulates to impregnate the other. Because the forces applied by the members 38 are substantially constant, the process for impregnation is repeatable. That is, the spherical members 38 remain in contact with the inner surfaces 140 and do not climb on top of each other as the device 10 is operating at normal speeds. Therefore, the forces acting on the particulates will be substantially constant.

In the illustrated embodiment, the turret 22 rotates about the first axis at a speed of about 1750 rpm and the first and second canisters 30 and 34 each rotate about the second and third axes, respectively, at a speed of about 2500 rpm. The canisters 30 and 34 are positioned such that the most distant point of the inner surfaces 140 of each canister 30 and 34 from the first axis is about 4.8 inches and each inner surface 140 defines a diameter of about 3.8 inches. The spherical members 44 are stainless steel balls each having a diameter of about 0.5 inches and a weight of about 0.29 oz. Therefore, in the illustrated embodiment the pressure applied to the particulates is:

| RPM | 100 | 500 | 875 | 1000 | 1200 | 1500 | 1750 |
|---|---|---|---|---|---|---|---|
| Pressure (lbs) | 0.025 | 0.627 | 1.919 | 2.506 | 3.609 | 5.639 | 7.676 |

In the illustrated embodiment, each ball 44 exerts a force of 7.676 lbs on the particulates as it rolls against the inner surface 140 of the respective canister 30 and 34. With 23 balls 44 in a single canister, arranged in 3 columns of 8, 7, 8 rolling side by side against the inner surface 140, at 1750 rpm, no particulate is ever exposed to more than 7,676 lbs of pressure at the rolling contact point between the ball 44 and inner surface 140. It should be appreciated, however, that centrifugal device 10 can have other configurations as desired. For example, the spherical members 44 can have other dimensions, the inner surfaces 140 can define other diameters, and the turret 22 and canisters 30 and 34 can rotate at other speeds as desired.

In one embodiment, the present invention can be used to make combination therapies that alter the defenses of cancerous cells to oxidative stress. One class of such therapies increases free radical availability to cancerous cells. A representative subclass of such therapies involve administration of pharmaceutical compositions comprising a tyrosine hydroxylase inhibitor, a melanin promoter, a p450 3A4 promoter, a leucine aminopeptidase inhibitor, and, optionally, a growth hormone inhibitor. Therefore at least one of the particulate materials retained by the first and second vessels 110 and 130 can include an active pharmaceutical ingredient or can have particles that individually comprise two or more active pharmaceutical ingredients.

While not intending to be bound by any particular mechanism of operation, at least one of the particulate materials can include a tyrosine hydroxylase inhibitor, which is believed to function by accumulating in cancer cells and preventing them from forming a coating of either lipids or hyaluronan. By preventing the cancer cells from forming a coating of either lipids or hyaluron, the cancer cells are believed to be made more accessible to oxidative stress. Representative tyrosine hydroxylase inhibitors include tyrosine derivatives, which typically are rapidly absorbed by most cancers and inflamed tissues. Representative tyrosine derivatives include one or more of methyl (2R)-2-amino-3-(2-chloro-4-hydroxyphenyl) propanoate, D-tyrosine ethyl ester hydrochloride, methyl (2R)-2-amino-3-(2,6-dichloro-3,4-dimethoxyphenyl) propanoate H-D-Tyr(TBU)-allyl ester HCl, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, H-D-tyr-OMe.HCl, D-tyrosine methyl ester HCl, H-D-Tyr-OMe-HCl, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr (3,5-$I_2$)—OSu, Fmoc-tyr(3-$NO_2$)—OH, and α-methyl-DL-tyrosine.

At least one of the particulate materials can include melanin, a melanin promoter, or a combination thereof. Melanin promoters are chemical compounds that increase the production and/or the activity of melanin. Increased melanin levels are believed to reduce inflammation (through, for example, suppression of TNF) and exclude the sequestered lymph system. Melanin also is a photo catalyst, and can therefore promote chemical reactions that generate free radicals which, in turn, can become accessible to cancer cells. Representative melanin promoters are methoxsalen and melanotan II.

At least one of the particulate materials can include tamoxifen, toremifene, fulvestrant, anastrozole, exemestane, letrozole, imatinib mesylate, dasatinib, nilotinib, bosutinib, lapatinib, gefitinib, erlotinib, temsirolimus, everolimus, vandetanib, vemurafenib, crizotinib, vorinostat, romidepsin, bexarotene, alitretinoin, tretinoin, bortezomib, carfilzomib, pralatrexate, sorafenib, sunitinib, pazopanib, regorafenib, cabozantinib, denileukin diftitox, ziv-aflibercept, cisplatin, cisplatinum, (cis-diamminedichloroplatinum(II)), carboplatin, oxaliplatin, benzyl isothiocyanate, acetylcholine, or dihydrotestosterone (DHT).

While the foregoing description and drawings represent the preferred embodiment of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one component may be used and/or interchanged with features described in another component. The presently disclosed embodiment is therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been discussed above and others will be apparent to those skilled in the art. For example, it should be appreciated that the first and second canisters 30 and 34 can be configured to retain any material and is not limited to spherical members 38, particulates including the active ingredients listed above, or even particulates at all.

What is claimed:
1. A centrifugal mixing device comprising:
a shaft assembly that includes:
    a shaft body that is elongate along a first axis and is configured to be operably coupled to a motor such that the motor rotates the shaft assembly about the first axis, and
    a first shaft pulley that is rigidly fixed to the shaft body; and
    a second shaft pulley that is rigidly fixed to the shaft body;
a turret that is rotatably coupled to the shaft body and includes:
    a first canister that has a first canister pulley and is rotatable about a second axis, and
    a second canister that has a second canister pulley and is rotatable about a third axis; and
    a turret pulley that is in communication with the second shaft pulley such that rotation of the shaft assembly causes the turret to rotate about the first axis; and
a first drive belt that is in communication with the first shaft pulley, the first canister pulley, and the second canister pulley such that rotation of the shaft assembly by the motor causes the first and second canisters to rotate about the second and third axes, respectively,
a transition member that is configured to transfer rotational motion of the shaft assembly to the turret and that includes a first transition pulley and a second transition pulley, wherein the device further comprises a second drive belt that is in communication with the second shaft pulley and the first transition pulley such that when the motor causes the second shaft pulley to rotate about the first axis the second drive belt drives the transition member to thereby rotate the first and second transition pulleys about a fourth axis;
wherein the first shaft pulley, the first canister pulley, and the second canister pulley are each sized such that an acceleration of at least 600 g is imposed on material retained in the first and second canisters when the motor rotates the shaft assembly about the first axis.

2. The centrifugal mixing device of claim 1, wherein rotation of the shaft assembly by the motor (i) causes the turret to rotate about the first axis in a first rotational and (ii) causes each of the first and second canisters to rotate about the second and third axes, respectively, in a second rotational direction that is opposite the first rotational direction.

3. The centrifugal mixing device of claim 1, wherein the first shaft pulley is fixed to the shaft body between the first and second canister pulleys.

4. The centrifugal mixing device of claim 1, wherein the turret further includes a first support and a second support, and wherein the first canister is rotatably coupled to the first and second supports on a first side of the shaft assembly and the second canister is rotatably coupled to the first and second supports on a second side of the shaft assembly.

5. The centrifugal mixing device of claim 4, wherein (i) the first canister includes a first canister shaft that is rotatably coupled to the first support, (ii) the second canister includes a second canister shaft that is rotatably coupled to the first support, and (iii) the first canister pulley is rigidly fixed to the first canister shaft and the second canister pulley is rigidly fixed to the second canister shaft.

6. The centrifugal mixing device of claim 5, wherein each canister comprises at least three substantially spherical members.

7. The centrifugal mixing device of claim 1, further comprising a third drive belt that is in communication with the second transition pulley and the turret pulley such that when the motor causes the first and second transition pulleys to rotate about the fourth axis, the third drive belt drives the turret pulley to thereby rotate the turret about the first axis.

8. The centrifugal mixing device of claim 1, wherein the turret pulley, the first and second transition pulleys, the first and second shaft pulleys and the first and second canister pulleys are each sized such that an acceleration of about 691 g is imposed on material retained in the first and second canisters when the motor rotates the shaft assembly.

9. The centrifugal mixing device of claim 1, further comprising the motor.

10. A method comprising the steps of:
providing a centrifugal mixing device that comprises:
a shaft assembly that includes:
a shaft body that is elongate along a first axis and is configured to be operably coupled to a motor such that the motor rotates the shaft assembly about the first axis, and
a first shaft pulley that is rigidly fixed to the shaft body; and
a turret that is rotatably coupled to the shaft body and includes:
a first canister that has a first canister pulley and is rotatable about a second axis, and
a second canister that has a second canister pulley and is rotatable about a third axis; and
a first drive belt that is in communication with the first shaft pulley, the first canister pulley, and the second canister pulley such that rotation of the shaft assembly by the motor causes the first and second canisters to rotate about the second and third axes, respectively,
wherein the first shaft pulley, the first canister pulley, and the second canister pulley are each sized such that an acceleration of at least 600 g is imposed on material retained in the first and second canisters when the motor rotates the shaft assembly about the first axis;
placing in said first canister at least three substantially spherical members, a first particulate material, and at least a second particulate material;
rotating the turret about the first axis in a first direction at a first rotational speed;
rotating the first canister about the second axis in a second direction opposite the first direction at a second rotational speed;
causing each spherical member to contact an inner surface within the first canister such that a substantially constant force is applied against the inner side surface as the turret rotates at the first rotational speed and as the first canister rotates at the second rotational speed;
causing the first and second particulates to move between the spherical members and inner surface such that at least one of the first and second particulates is impregnated by the other.

11. The method of claim 10, wherein said rotation of said turret and said first canister subjects its contents to an acceleration of at least 600 g.

12. The method of claim 10, wherein said rotation of said turret and said first canister subjects its contents to an acceleration of about 691 g.

13. The method of claim 10, wherein the first rotating step comprises rotating the turret about the first axis at a first rotational speed that is between about 100 rpm and about 1750 rpm and the second rotating step comprises rotating the first canister about the second axis at a second rotational speed that is between about 140 rpm and about 2550 rpm.

14. The method of claim 10, wherein the first rotating step comprises rotating the turret about the first axis at a first rotational speed that is about 1750 rpm and the second rotating step comprises rotating the first canister about the second axis at a second rotational speed that is about 2500 rpm.

15. The method of claim 10, further comprising the steps of:
placing in said second canister at least three substantially spherical members, a first particulate material, and at least a second particulate material;
rotating the second canister about the third axis in the second direction at a third rotational speed;
causing each spherical member to contact an inner surface within the second canister such that a substantially constant force is applied against the inner side surface as the turret rotates at the first rotational speed and as the second canister rotates at the third rotational speed;
causing the first and second particulates to move between the spherical members and inner surface such that at least one of the first and second particulates that is retained by the second canister is impregnated by the other.

16. The method of claim 15, further comprising driving the first and second canisters with the first drive belt so as to cause the first and second canisters to rotate about the second and third axes, respectively.

17. The method of claim 10, wherein the first causing step comprises causing each spherical member to contact the inner side surface so as to form a column of spherical members that extends from a bottom of the inner surface to a top of the inner surface.

18. The method of claim 10 wherein at least one of said particulate materials comprises an active pharmaceutical ingredient.

19. A method comprising the steps of:
providing a The method of claim 13 wherein the centrifugal mixing device that comprises a shaft assembly that includes:
- a shaft body that is elongate along a first axis and is configured to be operably coupled to a motor such that the motor rotates the shaft assembly about the first axis, and
- a first shaft pulley that is rigidly fixed to the shaft body; and
- a second shaft pulley that is rigidly fixed to the shaft body;

a turret that is rotatably coupled to the shaft body and includes:
- a first canister that has a first canister pulley and is rotatable about a second axis, and
- a second canister that has a second canister pulley and is rotatable about a third axis; and
- a turret pulley that is in communication with the second shaft pulley such that rotation of the shaft assembly causes the turret to rotate about the first axis; and a first drive belt that is in communication with the first shaft pulley, the first canister pulley, and the second canister pulley such that rotation of the shaft assembly by the motor causes the first and second canisters to rotate about the second and third axes, respectively, a transition member that is configured to transfer rotational motion of the shaft assembly to the turret and that includes a first transition pulley and a second transition pulley, wherein the device further comprises a second drive belt that is in communication with the second shaft pulley and the first transition pulley such that when the motor causes the second shaft pulley to rotate about the first axis the second drive belt drives the transition member to thereby rotate the first and second transition pulleys about a fourth axis;

wherein the first shaft pulley, the first canister pulley, and the second canister pulley are each sized such that an acceleration of at least 600 g is imposed on material retained in the first and second canisters when the motor rotates the shaft assembly about the first axis;

placing in said first canister at least three substantially spherical members, a first particulate material, and at least a second particulate material;

rotating the turret about the first axis in a first direction at a first rotational speed;

rotating the first canister about the second axis in a second direction opposite the first direction at a second rotational speed;

causing each spherical member to contact an inner surface within the first canister such that a substantially constant force is applied against the inner side surface as the turret rotates at the first rotational speed and as the first canister rotates at the second rotational speed;

causing the first and second particulates to move between the spherical members and inner surface such that at least one of the first and second particulates is impregnated by the other.

* * * * *